(12) United States Patent
Tu et al.

(10) Patent No.: US 12,371,398 B2
(45) Date of Patent: Jul. 29, 2025

(54) METHOD FOR PREPARING FORMAMIDE COMPOUNDS VIA HYDROGENATION OF CARBON DIOXIDE CATALYZED BY POROUS MATERIALS

(71) Applicant: FUDAN UNIVERSITY, Shanghai (CN)

(72) Inventors: Tao Tu, Shanghai (CN); Yaliang Shen, Shanghai (CN); Qingshu Zheng, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 764 days.

(21) Appl. No.: 17/754,104

(22) PCT Filed: Dec. 29, 2020

(86) PCT No.: PCT/CN2020/140480
§ 371 (c)(1),
(2) Date: Mar. 23, 2022

(87) PCT Pub. No.: WO2021/147622
PCT Pub. Date: Jul. 29, 2021

(65) Prior Publication Data
US 2022/0289666 A1     Sep. 15, 2022

(30) Foreign Application Priority Data
Jan. 24, 2020 (CN) .......................... 202010077178.1

(51) Int. Cl.
*C07C 231/10* (2006.01)
*B01J 31/20* (2006.01)
(Continued)

(52) U.S. Cl.
CPC ............. *C07C 231/10* (2013.01); *B01J 31/20* (2013.01); *B01J 31/2273* (2013.01);
(Continued)

(58) Field of Classification Search
None
See application file for complete search history.

(56) References Cited

U.S. PATENT DOCUMENTS

2018/0030009 A1* 2/2018 Ding ..................... C07C 231/10

FOREIGN PATENT DOCUMENTS

| CN | 105985254 A | 10/2016 |
| CN | 108558692 A | 9/2018 |

(Continued)

OTHER PUBLICATIONS

English translation of Tu et al. (CN 110483791) (Year: 2019).*
(Continued)

*Primary Examiner* — Renee Claytor
*Assistant Examiner* — Jennifer C Sawyer
(74) *Attorney, Agent, or Firm* — Bayramoglu Law Offices LLC

(57) ABSTRACT

A method for preparing formamide compounds via hydrogenation of carbon dioxide catalyzed by porous materials includes the following steps: by taking porous organometallic polymers as catalysts, reacting amine compounds with carbon dioxide and hydrogen under an air atmosphere to prepare formamide compounds. The method has the advantages of high reaction efficiency, good selectivity, mild conditions, economy, environmental protection, and simple operation. The catalysts are solid organometallic polymers with large specific surface area, strong carbon dioxide adsorption, hierarchical pore distribution, and uniformly dispersed metal centers. They are designed and synthesized as the reaction catalysts by changing the proportion of the cross-linked comonomer. The catalysts can be especially used for catalytic synthesis of fine chemical N, N-dimethylformamide (DMF) without addition of any additional (Continued)

solvent, alkali, or other additives, which is convenient for separation and purification of DMF.

14 Claims, 3 Drawing Sheets

(51) Int. Cl.
*B01J 31/22* (2006.01)
*C07F 15/00* (2006.01)

(52) U.S. Cl.
CPC ....... *C07F 15/0033* (2013.01); *B01J 2231/40* (2013.01); *B01J 2531/827* (2013.01)

(56) References Cited

FOREIGN PATENT DOCUMENTS

| | | |
|---|---|---|
| CN | 108623493 A | 10/2018 |
| CN | 108822243 A | 11/2018 |
| CN | 109553641 A | 4/2019 |
| CN | 110357770 A | 10/2019 |
| CN | 110483791 A | 11/2019 |

OTHER PUBLICATIONS

Michele Aresta, et al., Carbon Dioxide as Chemical Feedstock, 2010, pp. V- XIX, WILEY-VCH Verlag GmbH & Co.

Philip G. Jessop, et al., Catalytic Production of Dimethylformamide from Supercritical Carbon Dioxide, J. Am. Chem. Soc., 1994, pp. 8851-8852, vol. 116, No. 19.

Philip G. Jessop, et al., Homogeneous Catalysis in Supercritical Fluids: Hydrogenation of Supercritical Carbon Dioxide to Formic Acid, Alkyl Formates, and Formamides, J. Am. Chem. Soc., 1996, pp. 344-355, vol. 118, No. 2.

Yang Zhang, et al., N-Formylation of Amines with CO2 and H2 by Using NHC-Iridium Coordination Assemblies as Solid Molecular Catalysts, Chem. Asian J., 2018, pp. 3018-3021, vol. 13.

\* cited by examiner

METHOD FOR PREPARING FORMAMIDE COMPOUNDS VIA HYDROGENATION OF CARBON DIOXIDE CATALYZED BY POROUS MATERIALS

CROSS REFERENCE TO THE RELATED APPLICATIONS

This application is the national phase entry of International Application No. PCT/CN2020/140480, filed on Dec. 29, 2020, which is based upon and claims priority to Chinese Patent Application No. 202010077178.1, filed on Jan. 24, 2020, the entire contents of which are incorporated herein by reference.

TECHNICAL FIELD

The present invention belongs to the technical field of organic synthesis and heterogeneous catalysis, and particularly relates to a method for preparing formamide compounds.

BACKGROUND

Carbon dioxide is the most common greenhouse gas. About 800,000 years ago and at the beginning of the industrial revolution, its content in the atmosphere was about 280 ppm. Along with the overexploitation and utilization of fossil fuels (coal, petroleum and natural gas) and the large-scale decrease of forest vegetation, the carbon dioxide content in the atmosphere is getting higher and higher, and it is now about 400 ppm (this figure means that there are 400 carbon dioxide molecules in per million air molecules). Carbon dioxide, which strongly absorbs the long-wave radiation from the ground, can radiate long-wave radiation of longer wavelength to the ground, which plays a role in heat insulation for the ground. The increasing greenhouse effect has led to global warming, and results in a series of unpredictable global climate problems, such as "El Niño" and "La Niña" which are both considered to be related to the excessive carbon dioxide emissions. On the other hand, carbon dioxide is also considered as an abundant, cheap, non-toxic and renewable C1 resource. The conversion of carbon dioxide into desirable chemicals through chemical method can not only change the plight of long-term dependence on fossil fuels, but also effectively reduce the carbon dioxide content in the air, thereby helping to alleviate the greenhouse effect caused by carbon dioxide. Besides, applying carbon dioxide to replace the toxic and volatile acylation reagents, phosgene and carbon monoxide used in the traditional chemical industry is more in line with the concept of green chemistry [Carbon Dioxide as Chemical Feedstock, Ed.: Aresta, M.; Wiley-VCH, Weinheim, 2010.]. Therefore, chemists have been always committed to developing greener and more efficient methods to realize the resource utilization and energy utilization of carbon dioxide. However, carbon dioxide is a gas molecule which is quite stable in thermodynamics and kinetics, with the carbons staying in the highest oxidation state, which makes the transformation of carbon dioxide still very challenging. Until now, more than 90% of carbon dioxide is used for producing urea, inorganic carbonates, carbonate esters, polycarbonates, salicylic acids, etc., while there is relatively fewer carbon dioxide that is fixed and converted into other high value-added chemicals.

Formamides, a type of compounds widely used in organic synthesis, can be applied for synthesizing high-value heterocyclic compounds, biological intermediates and drugs. Formamides can also be used as Lewis base catalysts in hydrosilylation reactions and other reactions. In addition, the formyl group is a useful protective group for the amine functional group in peptide synthesis. The most widely accepted method for preparing various formamides is the N-formylation reaction of amine and formic acid in the presence of a catalyst, among which the synthesis of N,N-dimethylformamide (DMF) has attracted much attention. In addition to being an important "universal solvent", DMF is also widely used as an important intermediate in organic synthesis, medicine and pesticide industry for industrial production. The main method for the industrial synthesis of DMF involves the direct N-formylation with dimethylamine and carbon monoxide catalyzed by sodium methoxide. This production method has the advantages of wide sources of raw materials, applicability for large-scale continuous production, etc., making this method adopted by large-scale enterprises in the United States, Japan and China. However, the inevitable side reactions of this method in the actual production will bring several undesired by-products like monomethyl formamide (MMF), dimethyl acetamide (DMAC), formic acid and salt substances, such as sodium hydroxide, sodium formate, sodium bicarbonate and carbonic acid sodium. Thus, the termination at set intervals is necessary to remove solid deposits and maintain equipments. Moreover, this method still relies on large-scale consumption of non-renewable coal resources to produce DMF, which is detrimental to sustainable development. Based on the fact that carbon dioxide is a cheap, non-toxic and renewable C1 resource and hydrogen is the cleanest and most economical reducing agent, taking the perspective of sustainable development into consideration, employing the mixture of greenhouse gas carbon dioxide ($CO_2$) and hydrogen ($H_2$) as a formylation reagent to directly react with amines for the production of various formamides is undoubtedly a green and environmentally friendly way.

Carbon dioxide is of important economic value in preparing important industrial raw material and chemical reagent DMF through N-formylation in the presence of hydrogen and dimethylamine. Although there have been some related reports and studies, these methods are still suffering from the following disadvantages: (1) quite high pressure (up to 210 atm) is required, although the homogeneous catalytic system developed in the early stage can reach a turnover number (TON) of 420,000 [Jessop, P. G.; Hsiao, Y.; Ikariya, T.; Noyori, R. J. Am. Chem. Soc. 1994, 116, 8851-8852. Jessop. P G; Hsiao, Y; Ikariya. T; Noyori. R. J. Am. Chem. Soc. 1996, 118, 344-355.], a supercritical reaction conditions should be introduced, with the total pressure of the system up to 210 atm, which raises a high requirement for the reaction equipment, making the industrial production of DMF more difficult; (2) it needs to add alkali, solvent, reducing agent, etc.; (3) it is hard to recover the catalyst and difficult to separate DMF; (4) the catalytic efficiency is low, which is not favorable for the industrial production. In addition, these homogeneous catalytic systems mostly involve the use of air and water-sensitive and expensive phosphine ligands, the high cost of catalysts and complicated synthesis, making the practical operations quite difficult. Even if some stable heterogeneous N-heterocyclic carbene iridium polymers have been used in this reaction, they still require a high amount of catalyst (0.1 mol %), the catalytic efficiency is still not good, and the turnover number can only reach 730 [Zhang, Y.; Wang, J.; Zhu, H.; Tu, T. Chem. Asian J. 2018, 13, 3018-3021.], which is far from the requirement of industrial production.

Therefore, there is an urgent need in the field for catalytic materials with stable structures, convenient synthesis, high catalytic efficiency, good selectivity and wide substrate applicability to transform carbon dioxide into formamide compounds under mild conditions, especially for the reaction of the bulky fine chemical DMF, so as to lay a foundation for the further industrial application of this system.

SUMMARY

The present invention aims to provide a mild, convenient and efficient method for preparing formamide compounds via hydrogenation of carbon dioxide catalyzed by porous materials.

The method for preparing formamide compounds via hydrogenation of carbon dioxide catalyzed by porous materials provided herein comprises the following steps: by taking porous organometallic polymers as shown in formula (V) as catalysts, amine compounds, as shown in general formula (I), react with carbon dioxide and hydrogen under an air atmosphere to prepare a formamide compound as shown in general formula (II); the specific preparation steps are as below:

under an air atmosphere, adding the organic amine compound (I) and the catalyst (V) to a 125 mL autoclave, sealing the autoclave, and charging carbon dioxide and $H_2$ with a certain pressure; placing the reaction system in an oil bath, and then stirring and heating it to react for a certain period of time; slowly releasing the pressure after cooling down, and obtaining a formamide product by distillation or column separation;

the reaction formula is:

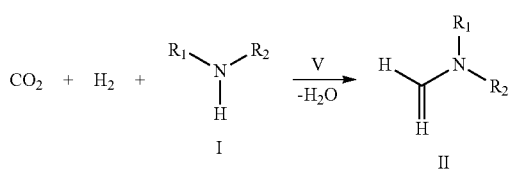

where:

$R_1$ is hydrogen, substituted or unsubstituted $C_1$-$C_{20}$ alkyl, substituted or unsubstituted $C_4$-$C_{10}$ cycloalkyl, substituted or unsubstituted $C_6$-$C_{24}$ aryl or heteroaryl, aryl alkyl or heteroaryl alkyl of substituted or unsubstituted $C_7$-$C_{25}$, —$(CH_2)$n-$OR_3$ or —$(CH_2)$n-$NR_4R_5$, wherein, n=1-8;

$R_2$ is substituted or unsubstituted $C_1$-$C_{20}$ alkyl, substituted or unsubstituted $C_4$-$C_{10}$ cycloalkyl, substituted or unsubstituted $C_6$-$C_{24}$ aryl or heteroaryl, substituted or unsubstituted $C_7$-$C_{25}$ aryl alkyl or heteroaryl alkyl, —$(CH_2)$n-$OR_3$ or —$(CH_2)$n-$NR_4R_5$, wherein, n=1-8, and $R_1$ and $R_2$ can be connected into substituted or unsubstituted $C_4$-$C_{10}$ cycloalkyl;

wherein, $R_3$, $R_4$ and $R_5$ are separately selected from: hydrogen, substituted or unsubstituted $C_1$-$C_{20}$ alkyl, substituted or unsubstituted $C_6$-$C_{24}$ aryl, and substituted or unsubstituted $C_7$-$C_{25}$ aryl alkyl or heteroaryl, wherein, $R_4$ and $R_5$ can be connected into substituted or unsubstituted $C_3$-$C_{10}$ cycloalkyl;

wherein, the "substituted" means that one or more hydrogen atoms in the group are substituted by a substituent selected from the following groups: halogen, $C_1$-$C_4$ alkyl, $C_1$-$C_4$ halogenated alkyl, $C_2$-$C_6$ alkenyl, $C_2$-$C_6$ alkynyl, $C_1$-$C_6$ alkoxy, hydroxyl, amino and sulfhydryl.

The porous organometallic polymer as shown in general formula (V) is:

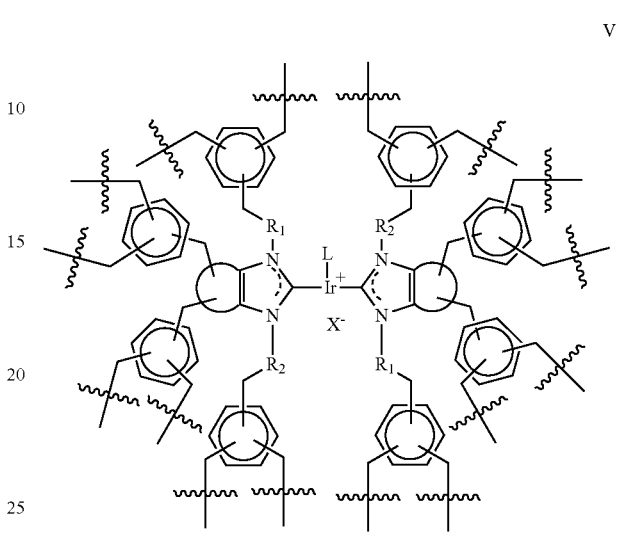

where:

=(hetero)aryl and functional group substituted (hetero)aryl;

the N-heterocyclic carbene ligands are benzimidazolylidene, phenanthromidazolylidene, acenaphthoimidazolylidene, pyrenoimidazolylidene, and bibenzimidazolylidene ligands;

X is halogen anion, tetrafluoroborate, hexafluorophosphate or hexafluoroantimonate;

L is an auxiliary ligand, and the auxiliary ligand is halogen, carbonyl, benzene ring, cyclopentene ring, cyclooctadiene, hydroxyl, water, carbonate, acetate, acetylacetone anion or phosphine ligand;

$R_1$ and $R_2$ are chain alkane groups with a carbon number of 1-12, and cyclic alkane groups, benzyl or aryl with a carbon number of 5-7.

The method for preparing formamide compounds in the present invention neither requires gloveboxes or other special equipment in the experimental operation, nor alkali or other additives in the reaction.

In the present invention, the amine compound is a primary organic amine or secondary organic amine compound.

In the present invention, the molar ratio of the organic amine compound to the catalyst is 1000-100,000:1, and preferably (5,000-20,000):1.

In the present invention, the reaction time is 2-160 hours, and preferably 2-48 hours.

In the present invention, the hydrogen pressure is controlled at 5-40 atm, and the carbon dioxide pressure is controlled at 5-40 atm, and preferably 30 atm for the hydrogen pressure and 30 atm for the carbon dioxide pressure.

In the present invention, the reaction temperature is 80-150° C., and preferably 80-120° C.

In the present invention, the reaction is carried out in an organic solvent which is selected from: DMF, tetrahydrofuran, 2-methyltetrahydrofuran, dioxane, glycol dimethyl ether, tert-butyl methyl ether, benzene, methylbenzene, xylene, methanol, ethanol, isopropanol, tert-butanol; or a combination of several of them, preferably methanol and tetrahydrofuran.

For the method for preparing formamide compounds proposed in the present invention, the specific steps are: under an air atmosphere, adding the organic amine compound, the catalyst (V) and the organic solvent to a 125 mL autoclave, sealing the autoclave, and charging carbon dioxide and hydrogen with a certain pressure; placing the reaction system in an oil bath, and then stirring and heating it to react for a certain period of time; slowly releasing the pressure after cooling down, and obtaining a formamide product by distillation or column separation.

In the present invention, when the amine compound is dimethylamine or its equivalent dimethylamine carbon dioxide salt, the product is DMF. At the moment, it is unnecessary to carry out the reaction in the organic solvent and add any alkali and other additives; the reaction formula is:

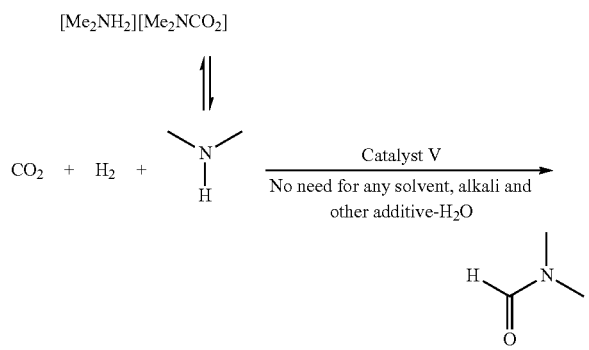

where:
the molar ratio of the dimethylamine equivalent, namely the dimethylamine carbon dioxide salt, to the catalyst is 1,000-100,000:1, and preferably (10,000-100,000):1.

The reaction time is 2-160 hours, and preferably 2-96 hours.

The hydrogen pressure is 5-40 atm, and the carbon dioxide pressure is 5-40 atm, and preferably 25-30 atm for the hydrogen pressure and 25-30 atm for the carbon dioxide pressure.

The reaction temperature is 80-150° C., and preferably 100-120° C.

It is unnecessary to dissolve the catalyst in DMF or other solvents when applied in the reaction, and the catalyst can be recovered by centrifugal filtration after the reaction is completed.

The recovered catalyst can be directly used in the next cycle without further activation steps.

The catalyst recovered by means of centrifugal filtration, etc. can be recycled for dozens of times and the stable catalytic activity and selectivity can be maintained still.

During the recycling, it is only necessary to add the recovered catalyst into the autoclave again, and repeat the above steps for reaction and post-treatment. In this way, the catalyst can be recycled for dozens of times and can still maintain the stable activity and selectivity.

In the present invention, the porous organometallic polymer material as a catalyst is prepared by the following method; the specific preparation steps are as follow: at room temperature, dissolving in the organic solvent a bis-carbene iridium compound shown by the general formula III and 3-9 equivalents of arene shown by the general formula IV, slowly adding a cross-linking agent and a Lewis acid catalyst under nitrogen atmosphere, and then sealing the mixture; placing the reaction system in an oil bath at 30-80° C. to react for 1-72 hours until the reaction stops; after cooling down, perform filtration, washing, Soxhlet extraction and vacuum drying to obtain the porous organometallic polymer materials shown by general formula V.

The reaction formula is:

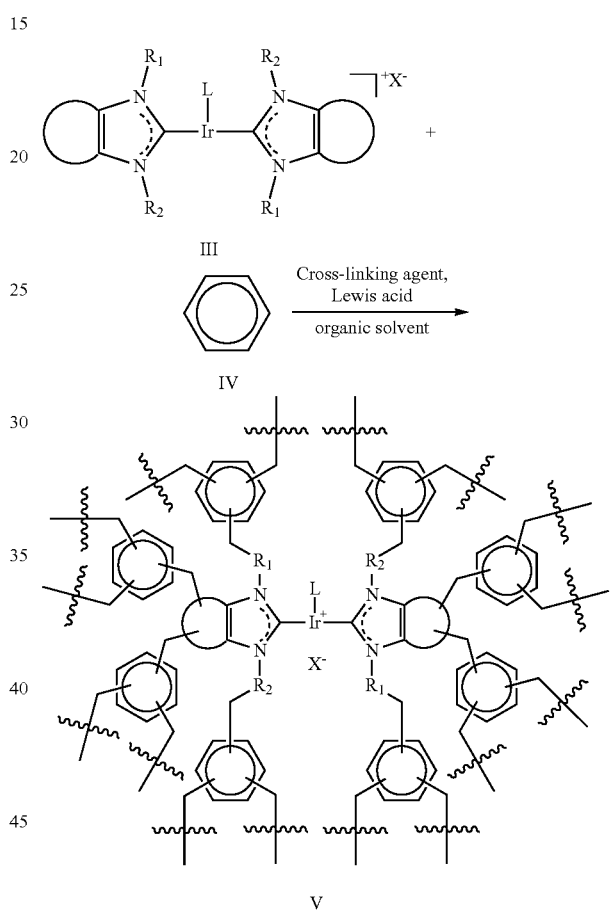

where:

=(hetero)aryl and functional group substituted (hetero) aryl;

The N-heterocyclic carbene ligands are benzimidazolylidene, phenanthromidazolylidene, acenaphthoimidazolylidene, pyrenoimidazolylidene, and bibenzimidazolylidene ligands;

X is halogen anion, tetrafluoroborate, hexafluorophosphate or hexafluoroantimonate;

L is an auxiliary ligand, and the auxiliary ligand is halogen, carbonyl, benzene ring, cyclopentene ring, cyclooctadiene, hydroxyl, water, carbonate, acetate, acetylacetone anion or phosphine ligand;

$R_1$ and $R_2$ are chain alkane groups with a carbon number of 1-12, and cyclic alkane groups, benzyl or aryl with a carbon number of 5-7.

In the present invention, the types of homogeneous catalyst precursor and comonomer are selected, and their ratio is changed to regulate and control the activity of the solid catalytic material.

Specifically, the mass ratio of the copolymerized aromatic compound IV to the homogeneous catalyst precursor III is (1-24):1; the mass ratio of the cross-linking agent to the homogeneous catalyst precursor III is (3-9):1.

The mass ratio of the cross-linking agent to the homogeneous catalyst precursor III is (1-100):1, and preferably (15-20):1.

In the present invention, the cross-linking agent is selected from: dimethoxymethane, trimethyl orthoformate, trimethyl orthoacetate, triethyl orthoformate, triisopropyl orthoformate, dichlorobenzene, dibromobenzene, 1,4-dibenzyl chloride, 1,4-dibenzyl bromide and carbon tetrachloride.

The organic solvent is selected from dichloromethane, chloroform, carbon tetrachloride and 1,2-dichloroethane, and preferably dimethoxymethane.

The Lewis acid is selected from iron chloride and aluminum chloride; the solvent is dichloromethane, chloroform, carbon tetrachloride and 1,2-dichloroethane; the preferable Lewis acid is iron chloride and aluminum chloride.

The porous organometallic polymer materials prepared and synthesized by direct knitting method in the present invention have the advantages of high stability, large specific surface area, strong carbon dioxide adsorption capability, hierarchical pore structure and uniformly dispersed metal centers; in addition, the catalytic activity of the materials can be regulated and controlled by adjusting the ratio of the comonomer. These catalytic materials are used in the catalytic conversion of the greenhouse gas carbon dioxide into formamide compounds (including DMF); the exclusion of toxic gas, high reaction selectivity, water as the only by-product, mild reaction conditions, no need for special equipment and simple operation, all make this conversion conforming to the concepts of green, economic and sustainable development. Especially in the preparation of bulk chemical DMF, even when the amount of catalyst is less than 0.0001 mol %, the high-efficiency conversion of carbon dioxide into DMF can be still realized, with a maximum turnover number (TON) up to 1,581,588. In addition, the reaction does not require any additional solvent, alkali and other additive, which not only reduces the production cost of formamide compounds (including DMF), but also favors the separation and purification of the final product DMF due to the insolubility of solid porous organometallic polymer materials in DMF and other solvents. The catalyst recovered by simple centrifugation and filtration can be directly used in the next cycle without additional activation steps, and the catalyst can be recycled for dozens of times with maintained high activity and high selectivity.

The term "conversion efficiency" (or efficiency) used herein refers to the ratio (percentage) of the amount of a reactant consumed in a chemical reaction to the total amount of the reactant initially added. The conversion efficiency in the present invention is calculated based on dimethylamine.

The term "turnover number" used herein refers to the ratio of the number of converted moles of a reactant to the number of moles of a catalyst within a certain period of time. The turnover number in the present invention is calculated based on dimethylamine.

In the present invention, the conversion efficiency and the turnover number are calculated based on $^1$H NMR or separation results.

DETAILED DESCRIPTION OF THE EMBODIMENTS

In order to make the objectives, technical solutions and advantages of the present invention clearer, the embodiments of the present invention will be described in detail as follows. However, those of ordinary skill in the art will understand that various technical details are proposed in the embodiments of the present invention for the readers to better understand the application. However, even without these technical details and various changes and modifications based on the following embodiments, the technical solutions to be protected by the claims of this application can be realized as well.

Embodiment 1: Synthesis of a Porous Organometallic Polymer Material 1a

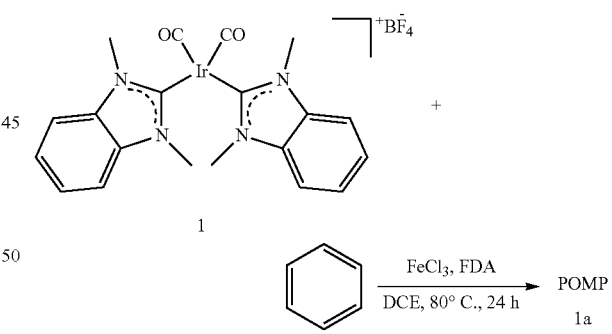

Figure 1:
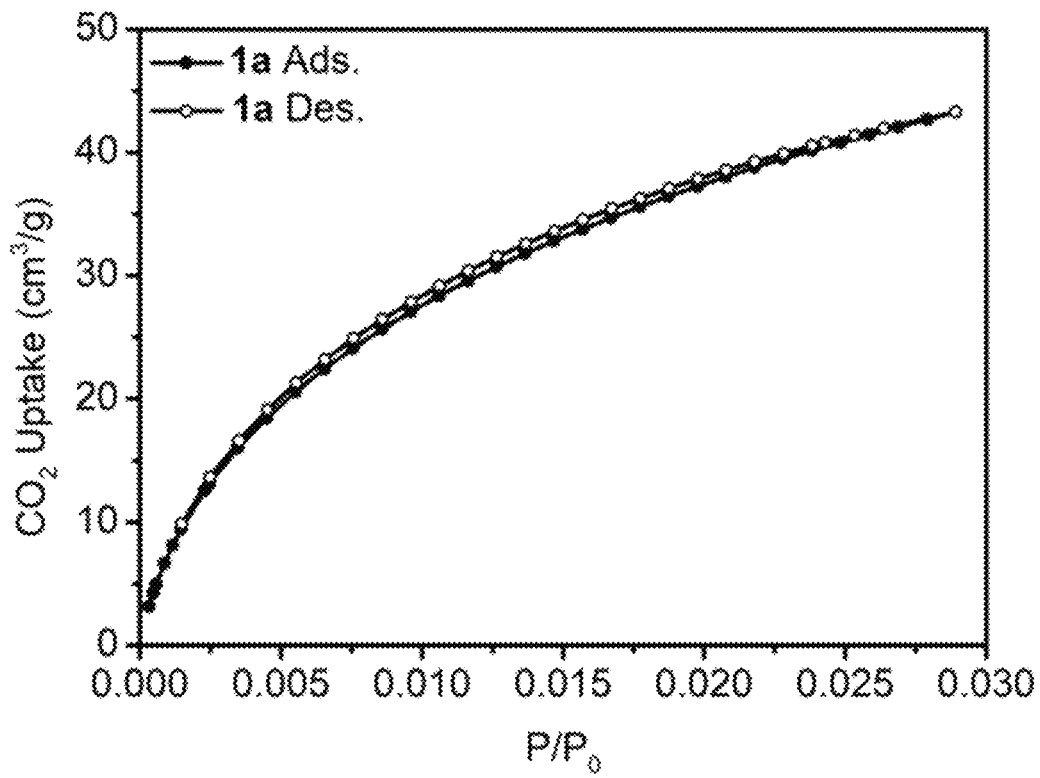
FIG. 1 shows the carbon dioxide adsorption profile of a porous organometallic polymer material 1a prepared in Embodiment 1.

1 mmol of bisbenzimidazolylidene iridium compound (0.63 g) was added into a 50 mL Schlenk tube, vacuumized and purged three times with nitrogen; then 10 mL of 1,2-dichloroethane and 3 mmol of benzene (0.23 g) were added in sequence; the mixture was stirred for a period of time at a room temperature until the solid was completely dissolved; 20 mmol of dimethoxy methane (FDA, 1.52 g) and anhydrous ferric chloride (3.24 g) were added. After being sealed, the reaction system was placed in an 80° C. oil bath to react for 24 hours. After the reaction was completed, the solution was cooled to the room temperature, filtered and washed; the resulting solid was subjected to Soxhlet extraction for 24 hours, and vacuum dried at 60° C. for 24 hours to obtain a porous organometallic polymer POMP 1a. The carbon dioxide adsorption profile of the solid is as shown in FIG. 1. Yield: 0.99 g, 90%.

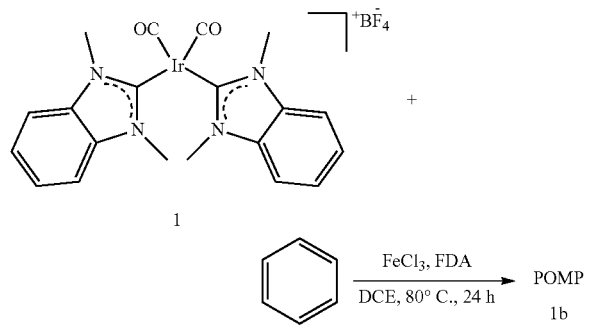

Figure 2:
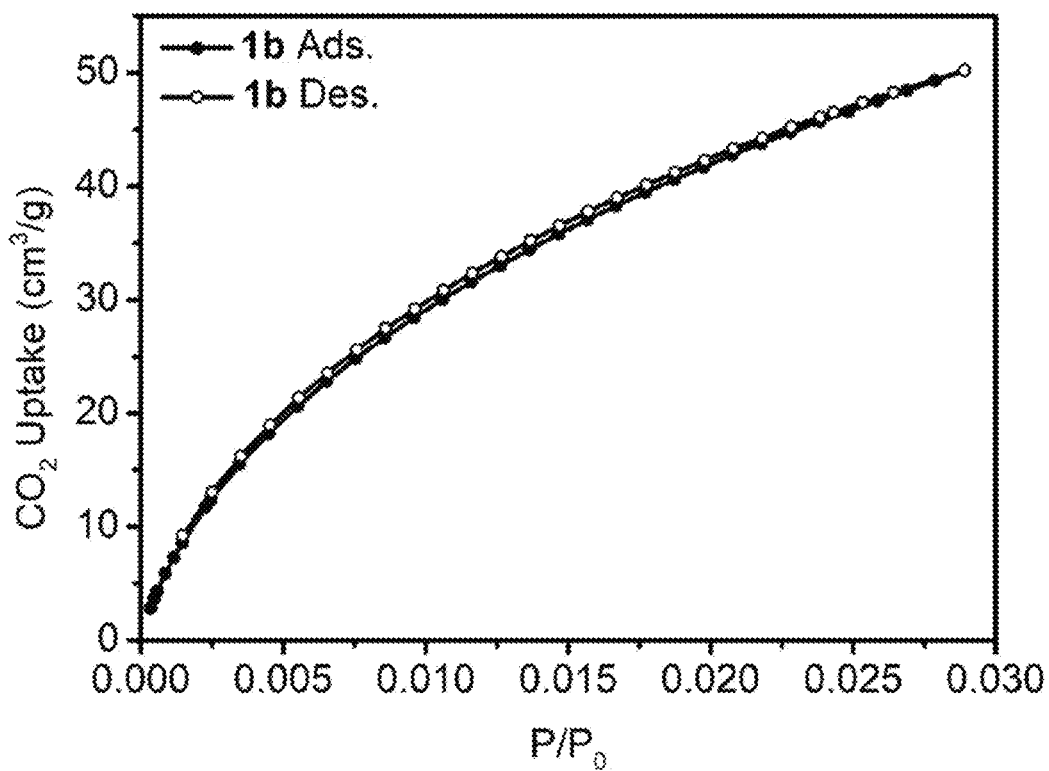
FIG. 2 shows the carbon dioxide adsorption profile of a porous organometallic polymer material 1b prepared in Embodiment 2.

Embodiment 2: Synthesis of a Porous Organometallic Polymer Material 1b 1 mmol of bisbenzimidazolylidene iridium compound (0.63 g) was added into a 50 mL Schlenk tube, vacuumized and purged three times with nitrogen; then 10 mL of 1,2-dichloroethane and 6 mmol of benzene (0.46 g) were added in sequence; the mixture was stirred for a period of time at a room temperature until the solid was completely dissolved; 20 mmol of dimethoxy methane (FDA, 1.52 g) and anhydrous ferric chloride (3.24 g) were added. After being sealed, the reaction system was placed in an 80° C. oil bath to react for 24 hours. After the reaction was completed, the solution was cooled to the room temperature, filtered and washed; the resulting solid was subjected to Soxhlet extraction for 24 hours, and vacuum dried at 60° C. for 24 hours to obtain a porous organometallic polymer POMP 1b. The carbon dioxide adsorption profile of the solid is as shown in FIG. 2. Yield: 1.17 g, 88%.

Embodiment 3: Synthesis of a Porous Organometallic Polymer Material 1c

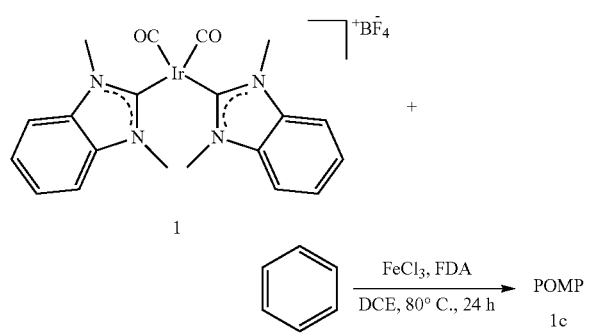

Figure 3:
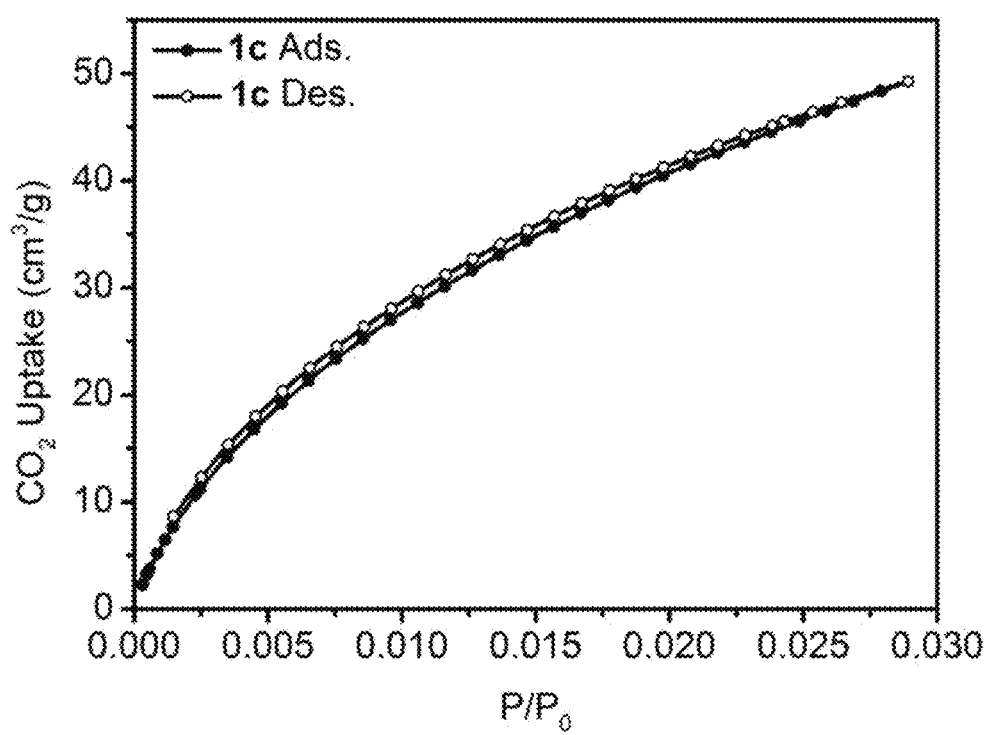
FIG. 3 shows the carbon dioxide adsorption profile of a porous organometallic polymer material 1c prepared in Embodiment 3.

1 mmol of bisbenzimidazolylidene iridium compound (0.63 g) was added into a 50 mL Schlenk tube, vacuumized and purged three times with nitrogen; then 10 mL of 1,2-dichloroethane and 9 mmol of benzene (0.70 g) were added in sequence; the mixture was stirred for a period of time at a room temperature until the solid was completely dissolved; 20 mmol of dimethoxy methane (FDA, 1.52 g) and anhydrous ferric chloride (3.24 g) were added. After being sealed, the reaction system was placed in an 80° C. oil bath to react for 24 hours. After the reaction was completed, the solution was cooled to the room temperature, filtered and washed; the resulting solid was subjected to Soxhlet extraction for 24 hours, and vacuum dried at 60° C. for 24 hours to obtain a porous organometallic polymer POMP 1c. The carbon dioxide adsorption profile of the solid is as shown in FIG. 3. Yield: 1.37 g, 87%.

Embodiment 4: Effect of Different Temperatures on Catalyzing Dimethylamine Formylation Reaction with a Porous Organometallic Polymer Material 1b

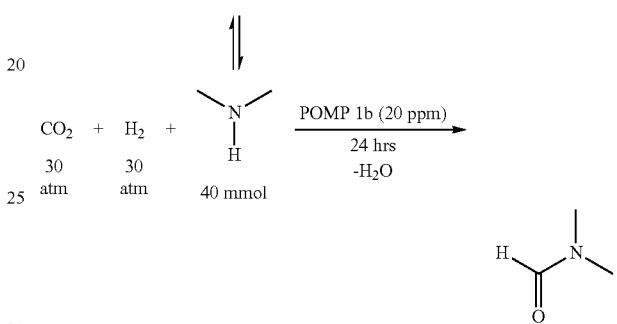

Under an air atmosphere, the dimethylamine carbon dioxide salt (40 mmol, 5.36 g, 4 mL) and a solid catalyst POMP 1b (20 ppm, 38 mg) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan at a set temperature for 24 hours. Upon completion of the reaction, the autoclave was cooled down to the room temperature, and the pressure was released slowly. 20 mL of methanol was added, and then mesitylene (240 mg, 2 mmol) was added into the reaction system as an internal standard for $^1$H NMR analysis to determine the yield. (See Table 1 for the results).

TABLE 1

Effect of Different Temperatures on Catalyzing Dimethylamine Formylation Reaction with a Porous Organometallic Polymer Material 1b

| Temperature (° C.) | 60 | 80 | 100 | 120 | 140 |
|---|---|---|---|---|---|
| Yield (%) | 0 | 23 | 59 | 99 | 99 |

In the above table, the yields of DMF are all determined by $^1$H NMR with mesitylene as the internal standard.

It may be known from Table 1 that the changes in temperature had a significant effect on the results of the reaction. When the temperature was lower than 60° C., no reaction would occur. The yield increased significantly as the temperature rose. When the reaction temperature was 120° C., the yield could reach a quantitative level, and the quantitative yield could be obtained still by increasing the temperature. Considering energy consumption and practical industrial applications, the optimal reaction temperature is 120° C.

Embodiment 5: Effect of Carbon Dioxide and Hydrogen Pressures on Catalyzing Dimethylamine Formylation Reaction with a Porous Organometallic Polymer Material 1b

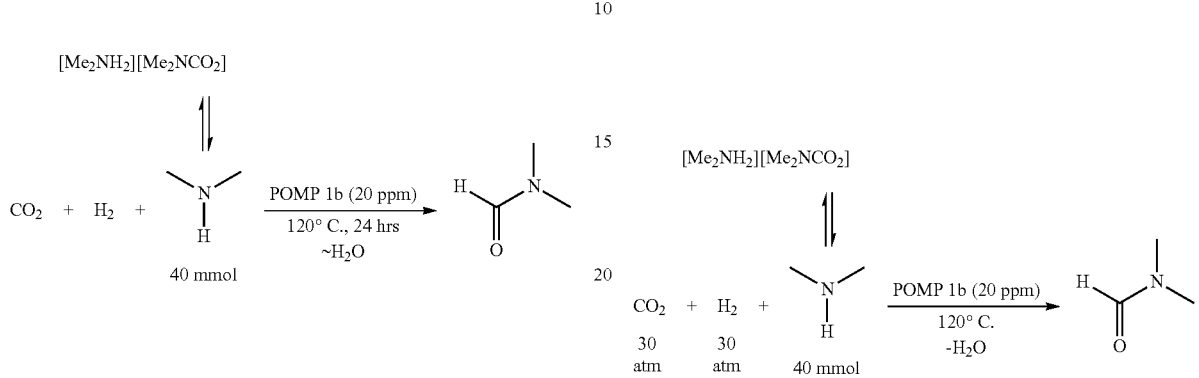

Under an air atmosphere, the dimethylamine carbon dioxide salt (40 mmol, 5.36 g, 4 mL) and a solid catalyst POMP 1b (20 ppm, 38 mg) were added into a stainless steel autoclave with a magnetic stir bar. The autoclave was tightened, purged three times with carbon dioxide, charged with carbon dioxide of a certain pressure, and then charged with hydrogen of a certain pressure. Afterwards, the reaction system was stirred in an oil bath pan of 120° C. for 24 hours. Upon completion of the reaction, the autoclave was cooled down to the room temperature, and the pressure was released slowly. 20 mL of methanol was added, and then mesitylene (240 mg, 2 mmol) was added into the reaction system as an internal standard for $^1$H NMR analysis to determine the yield. The results are shown in Table 2:

TABLE 2

Effect of Carbon Dioxide and Hydrogen Pressures on Catalyzing Dimethylamine Formylation Reaction with a Porous Organometallic Polymer Material 1b

| Carbon Dioxide Pressures (atm) | 10 | 20 | 30 | 40 |
|---|---|---|---|---|
| Hydrogen Pressures (atm) | 10 | 20 | 30 | 40 |
| $^1$H NMR Yield (%) | 10 | 56 | 99 | 99 |

In the above table, the yields of DMF are all determined by $^1$H NMR with mesitylene as the internal standard.

It may be known from Table 2 that carbon dioxide and hydrogen pressures had a great effect on the results of the reaction. The increases in carbon dioxide and hydrogen pressures were favorable for the conversion of carbon dioxide into DMF. In the selected pressure, when the partial pressures of carbon dioxide and hydrogen were both 30 atm, the quantitative preparation of DMF could be achieved. Further increases in the pressures could still achieve the high-selectivity preparation of DMF without excessive hydrogenation and other by-products. Considering safety and practical industrial applications, the optimal carbon dioxide and hydrogen pressures are 30 atm/30 atm.

Embodiment 6: Effect of Different Reaction Times on Catalyzing Dimethylamine Formylation Reaction with a Porous Organometallic Polymer Material 1b Under an air atmosphere, dimethylamine carbon dioxide salt (40 mmol, 5.36 g, 4 mL) and a solid catalyst POMP 1b (20 ppm, 38 mg) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for a certain period of time. Upon completion of the reaction, the autoclave was cooled down to the room temperature, and the pressure was released slowly. 20 mL of methanol was added, and then mesitylene (240 mg, 2 mmol) was added into the reaction system as an internal standard for $^1$H NMR analysis to determine the yield. The results are shown in Table 3:

TABLE 3

Effect of Different Reaction Times on Catalyzing Dimethylamine Formylation Reaction with a Porous Organometallic Polymer Material 1b

| Time (h) | 2 | 6 | 12 | 24 | 48 |
|---|---|---|---|---|---|
| Yield (%) | 5 | 18 | 49 | 99 | 99 |

In the above table, the yields of DMF are all determined by H NMR with mesitylene as the internal standard.

It may be known from Table 3 that the reaction time had a great effect on the results of the reaction. The reaction started slowly, and almost no reaction occurred in the first two hours. The reaction yield increased over time. When the reaction time reached 24 hours, DMF could be obtained in a quantitative yield, no excessive hydrogenation by-products would occur by further extending the reaction time, and the catalytic system exhibited a good selectivity. Considering energy consumption and actual industrial applications, the optimal reaction time is 24 hours.

Embodiment 7: Effect of Different Catalysts on Catalyzing Dimethylamine Formylation Reaction with a Porous Organometallic Polymer Material 1b

[Me$_2$NH$_2$][Me$_2$NCO$_2$]

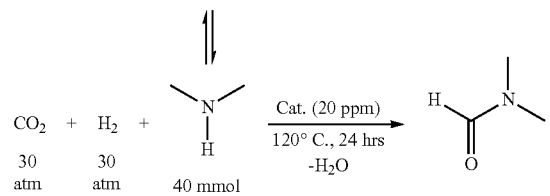

Under an air atmosphere, the dimethylamine carbon dioxide salt (40 mmol, 5.36 g, 4 mL) and a catalyst (20 ppm) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. 20 mL of methanol was added, and then mesitylene (240 mg, 2 mmol) was added into the reaction system as an internal standard for $^1$H NMR analysis to determine the yield. The results are shown in Table 4:

TABLE 4

Effect of Different Catalysts on Dimethylamine Formylation Reaction

| Catalyst | Homogeneous Catalyst 1 | POMP 1a | POMP 1b | POMP 1c |
|---|---|---|---|---|
| Yield (%) | 20 | 53 | 99 | 42 |

In the above table, the yields of DMF are all determined by $^1$H NMR with mesitylene as the internal standard.

It may be known from Table 4 that among the catalysts investigated, the solid porous organometallic polymer materials formed by the direct super-crosslinking method exhibited a activity better than that of the homogeneous catalyst precursor in this reaction. In the solid catalysts formed at several different copolymer ratios, when the ratio of homogeneous catalyst precursor 1 to benzene was 1:6, the resulting catalytic material could catalyze the conversion of carbon dioxide into DMF more efficiently, the activity of the resulting catalytic material would become worse by reducing or increasing equivalent weight of benzene, and thus the porous organometallic polymer material POMP 1b was preferred as the catalyst.

Embodiment 8: Effect of Different Catalyst Dosages on Catalyzing Dimethylamine Formylation Reaction with POMP 1b

[Me$_2$NH$_2$][Me$_2$NCO$_2$]

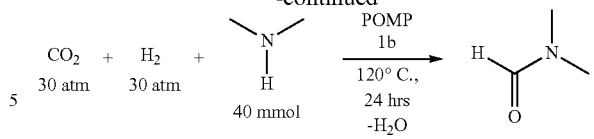

Under an air atmosphere, the dimethylamine carbon dioxide salt (40 mmol, 5.36 g, 4 mL) and a certain amount of a solid catalyst POMP 1b were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. 20 mL of methanol was added, and then mesitylene (240 mg, 2 mmol) was added into the reaction system as an internal standard for $^1$H NMR analysis to determine the yield. The results are shown in Table 5:

TABLE 5

Effect of Different Catalyst Dosages on Catalyzing Dimethylamine Formylation Reaction with POMP 1b

| POMP 1b (mol %) | 005 | 002 | 001 | 0005 |
|---|---|---|---|---|
| Yield (%) | 99 | 99 | 99 | 68 |
| TON | 20000 | 50000 | 100000 | 136000 |
| TOF(h$^{-1}$) | 833 | 2083 | 4167 | 5667 |

In the above table, the yields of DMF are all determined by $^1$H NMR with mesitylene as the internal standard.

It may be known from Table 5 that POMP 1b exhibited a very high catalytic activity in the reaction of the catalytic conversion of carbon dioxide into DMF. Even if the catalytic amount was as low as 0.001 mol % (1/100,000 molar equivalent), the yield of DMF could still reach the quantitative amount. When the catalytic amount was further reduced to 0.0005 mol % (5% molar equivalent), after 24 hours of reaction, although the yield decreased to 68%, the turnover number increased to 136,000 and the TOF also increased to 5667 h$^{-1}$. Therefore, reducing the catalyst dosage is favorable for improving the catalytic efficiency of POMP 1b.

Embodiment 9: Dimethylamine Formylation Reaction Catalyzed with a POMP 1b of 1/1,670,000 Molar Equivalent

[Me$_2$NH$_2$][Me$_2$NCO$_2$]

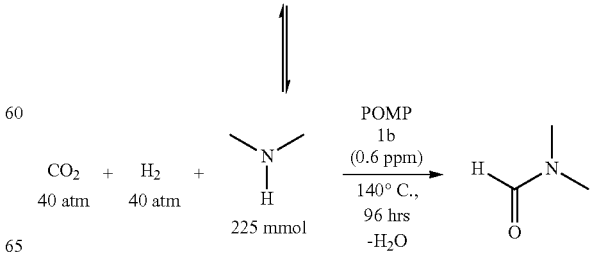

Under an air atmosphere, the dimethylamine carbon dioxide salt (115 mmol, 15.08 g, 23 mL) and the solid catalyst POMP 1b (0.6 ppm, 3.2 mg) were added into a stainless steel autoclave with a magnetic stir bar. The autoclave was tightened, purged three times with carbon dioxide, charged with 40 atm of carbon dioxide, and then charged with 40 atm hydrogen until a total pressure reaches 80 atm. Afterwards, the reaction system was stirred in an oil bath pan of 140° C. for 96 hours. It was unnecessary to supplement carbon dioxide or hydrogen during the reaction. Upon completion of the reaction, the autoclave was cooled down to the room temperature, and the pressure was released slowly. The liquid in the system was transferred to a round-bottomed flask, and 19.5 g of colorless liquid, a mixture of DMF and water, was obtained by means of vacuum distillation (80° C., 3.1 torr) ($^1$H NMR analysis showed that the water content was usually 7%-16%, and the yield was calculated based on a water content of 20%). The reaction yield was 95%, and the corresponding turnover number (TON) was 1,581,588.

Embodiment 10: Dimethylamine Formylation Reaction Catalyzed with a POMP 1b of 1/4,000,000 Molar Equivalent

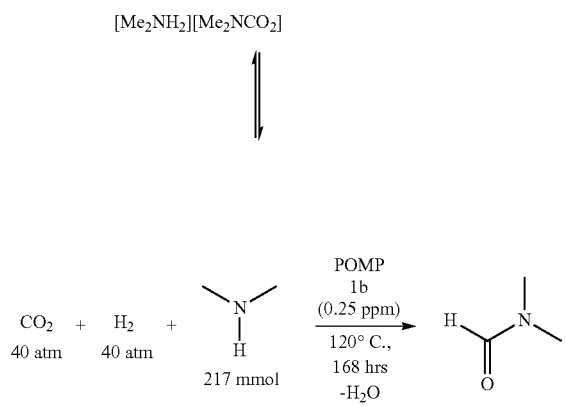

Under an air atmosphere, the dimethylamine carbon dioxide salt (110 mmol, 14.54 g, 23 mL) and a solid catalyst POMP 1b (0.25 ppm, 1.3 mg) were added into a stainless steel autoclave with a magnetic stir bar. The autoclave was tightened, purged three times with carbon dioxide, charged with 40 atm of carbon dioxide, and then charged with 40 atm hydrogen until a total pressure reaches 80 atm. Afterwards, the reaction system was stirred in an oil bath pan of 120° C. for 168 hours. It was unnecessary to supplement carbon dioxide or hydrogen during the reaction. Upon completion of the reaction, the autoclave was cooled down to the room temperature, and the pressure was released slowly. The liquid in the system was transferred to a round-bottomed flask, and 4.2 g of colorless liquid, a mixture of DMF and water, was obtained by means of vacuum distillation (80° C., 3.1 torr) ($^1$H NMR analysis showed that the water content was usually 7%-16%, and the yield was calculated based on a water content of 20%). The reaction yield was 21%, and the corresponding turnover number (TON) was 840,000.

Embodiment 11: Dimethylamine Formylation Reaction Catalyzed with a POMP 1b of 1/50,000 Molar Equivalent and the Recycling of Catalyst 1b

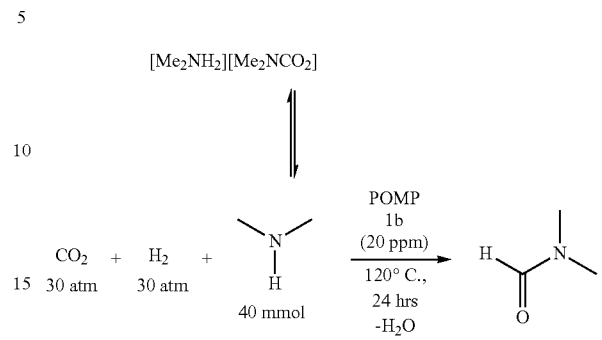

Under an air atmosphere, the dimethylamine carbon dioxide salt (40 mmol, 5.36 g, 4 mL) and a solid catalyst POMP 1b (20 ppm, 38 mg) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly.

Afterwards, the resulting liquid was transferred to a centrifuge tube, and the supernatant subjected to simple centrifugal separation was poured into a round bottom flask, with the catalyst remaining in the centrifuge tube. The steps were repeated 3-4 times until DMF was completely separated into the round-bottomed flask. 3.7 g of colorless liquid, a mixture of DMF and water, was obtained by vacuum distillation (80° C., 3.1 torr) ($^1$H NMR analysis showed that the water content was usually 7%-16%, and the yield was calculated based on a water content of 20%). The reaction yield was 99%. After being dried, the catalyst in the centrifuge tube was put into a 125 mL autoclave, and the above steps were repeated for the next round of dimethylamine formylation reaction. No additional activation steps were required for the catalyst.

Figure 4:
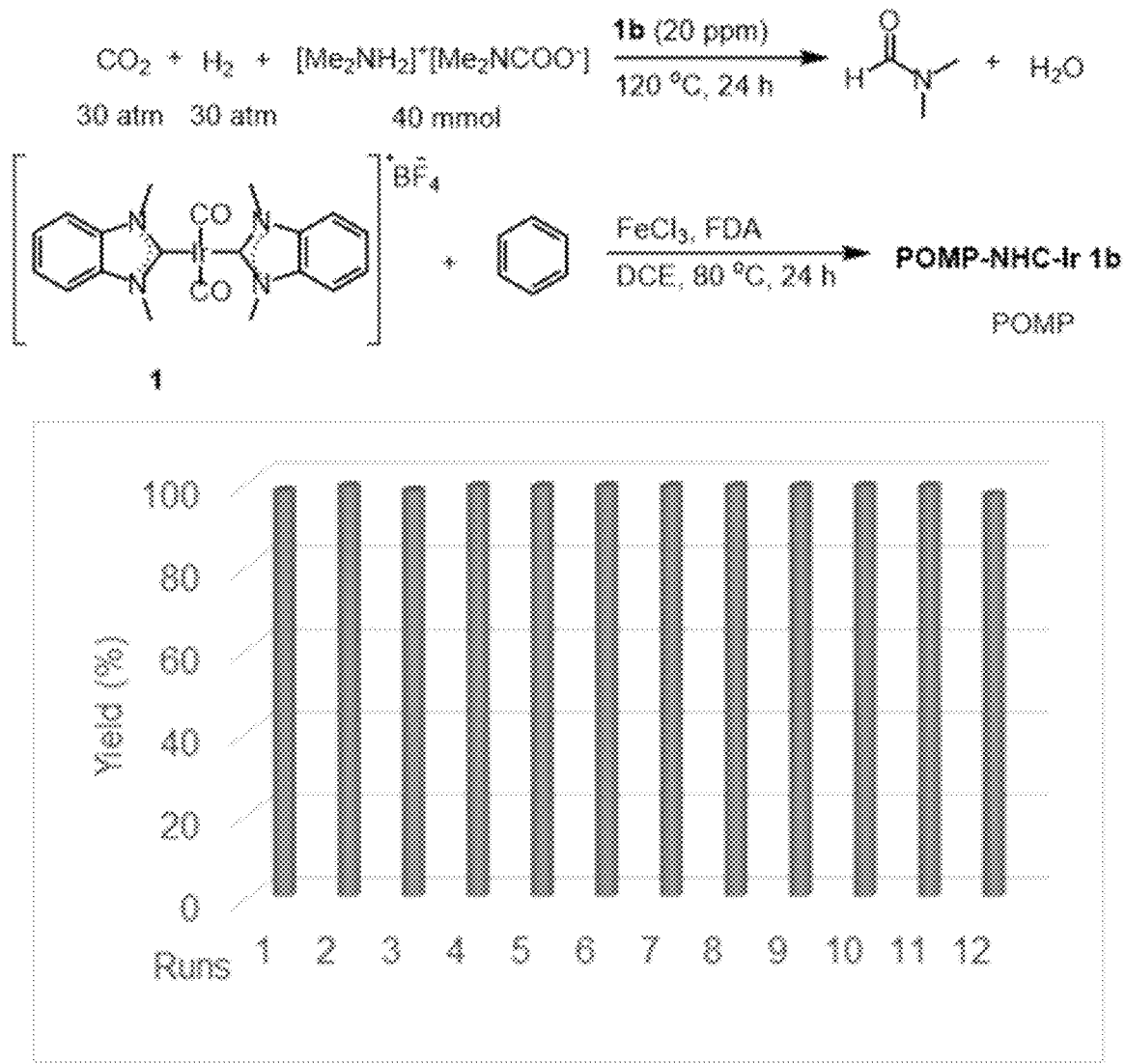
FIG. 4 shows the cyclic performance test of a catalyst 1b provided in Embodiment 11 in the dimethylamine formylation reaction.

Through the simple centrifugal separation operation, the catalyst could be recycled for more than 12 times, while the catalytic activity and selectivity were still maintained at a quantitative level (see FIG. 4).

Embodiment 12: Morpholine Formylation Reaction Catalyzed with a POMP 1b of 1/10,000 Molar Equivalent

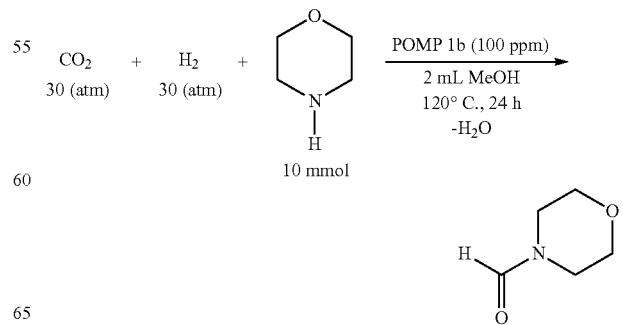

Under an air atmosphere, the morpholine (10 mmol, 0.87 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (1.15 g) of N-formylmorpholine, with a yield of up to 99%.

$^1$H NMR (400 MHz, CDCl$_3$) δ 7.97 (s, 1H), 3.12 (t, J=6.0, 4H), 1.64 (s, 4H) ppm; $^{13}$C NMR (100 MHz, DMSO) δ 161.4, 67.2, 66.2, 45.5, 40.3 ppm.

Embodiment 13: N-Phenylpiperazine Formylation Reaction Catalyzed with a POMP 1b of 1/10,000 Molar Equivalent

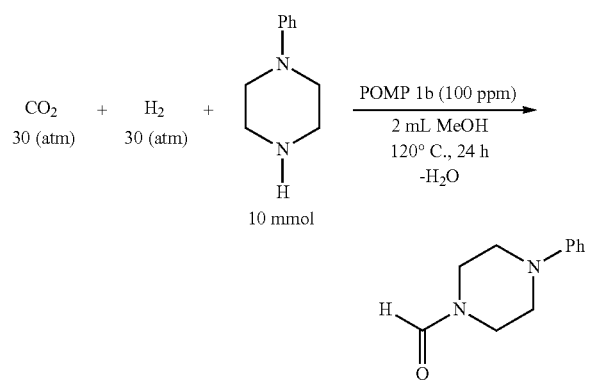

Under an air atmosphere, the N-phenylpiperazine (10 mmol, 1.62 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a white solid (1.90 g) of N-phenyl-N-formylpiperazine, with a yield of up to 99%.

$^1$H NMR (400 MHz, DMSO) δ 8.08 (s, 1H), 7.23 (t, J=7.8 Hz, 2H), 6.97 (d, J=8.4 Hz, 2H), 6.83 (d, J=7.2 Hz, 1H), 3.50 (q, J=4.5 Hz, 4H), 3.14 (t, J=5.2 Hz, 2H), 3.08 (t, J=5.2 Hz, 2H) ppm;

$^{13}$C NMR (100 MHz, DMSO) δ 161.3, 151.3, 129.4, 120.0, 116.7, 49.9, 48.7, 45.0 ppm.

Embodiment 14: Piperidine Formylation Reaction Catalyzed with a POMP 1b of 1/10,000 Molar Equivalent

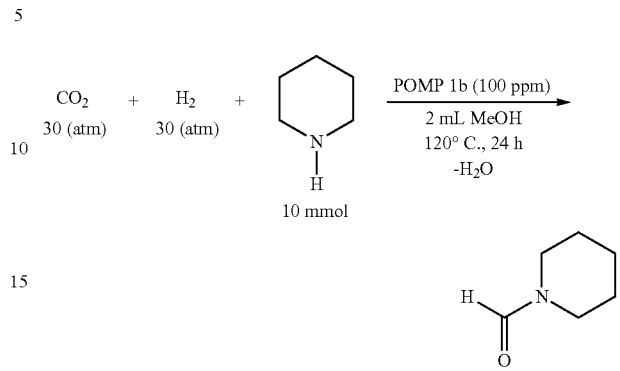

Under an air atmosphere, the piperidine (10 mmol, 0.85 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (1.04 g) of N-formylpiperidine, with a yield of up to 92%.

$^1$H NMR (400 MHz, CDCl$_3$) δ 8.62 (major isomer, s, 0.84H), 8.00 (minor isomer, s, 0.25H), 3.02 (t, J=6.0 Hz, 4H), 1.78 (d, J=5.6 Hz, 4H), 1.643-1.629 (m, 2H) ppm.

Embodiment 15: Diethylamine Formylation Reaction Catalyzed with a POMP 1b of 1/10,000 Molar Equivalent

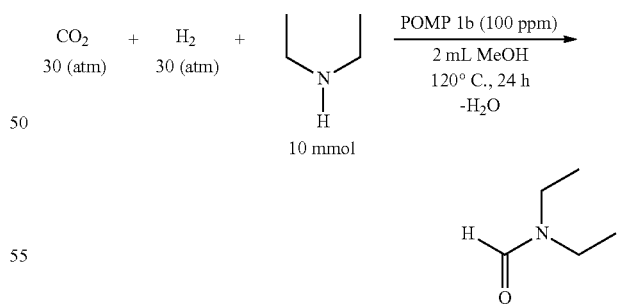

Under an air atmosphere, the diethylamine (10 mmol, 0.73 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (0.84 g) of N-diethylformamide, with a yield of up to 83%.

$^1$H NMR (400 MHz, CDCl$_3$) δ 7.77 (s, 1H), 3.09-3.03 (m, 4H), 0.94-0.85 (m, 6H) ppm; $^{13}$C NMR (100 MHz, CDCl$_3$) δ 162.0, 41.6, 36.3, 14.7, 12.5 ppm.

Embodiment 16: Diethanolamine Formylation Reaction Catalyzed with a POMP 1b of 1/10,000 Molar Equivalent

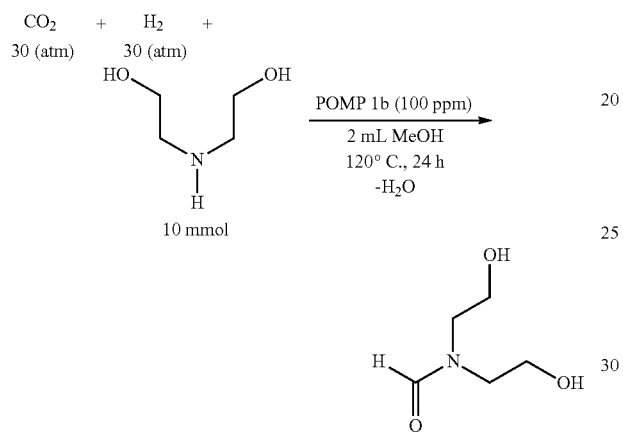

Under an air atmosphere, the diethanolamine (10 mmol, 1.05 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (1.21 g) of N-di(2-hydroxyethyl)formamide, with a yield of up to 91%.

$^1$H NMR (400 MHz, CDCl$_3$) δ 8.15 (s, 1H) 3.91 (t, J=4.8 Hz, 2H), 3.78 (t, J=4.8 Hz, 2H), 3.53 (t, J=4.8 Hz, 2H), 3.44 (t, J=4.8, 2H) ppm.

Embodiment 17: Cyclohexylamine Formylation Reaction Catalyzed with a POMP 1b of 1/10,000 Molar Equivalent

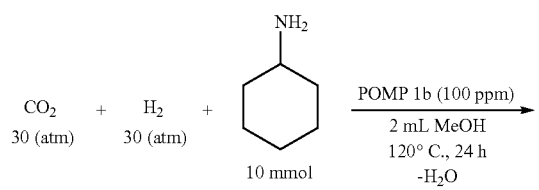

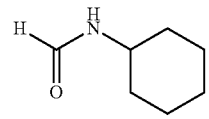

Under an air atmosphere, the cyclohexylamine (10 mmol, 0.99 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (1.02 g) of N-formylcyclohexylamine, with a yield of up to 80%.

$^1$H NMR (400 MHz, DMSO) δ 7.91 (s, 1H), 3.59 (d, J=8.0 Hz, 1H), 1.70 (t, J=9.6 Hz, 4H), 1.53 (q, J=3.2 Hz, 1H), 1.28-1.13 (m, 5H) ppm; $^{13}$C NMR (100 MHz, DMSO) δ 160.4, 46.5, 32.7, 25.6, 24.8 ppm.

Embodiment 18: Benzylamine Formylation Reaction Catalyzed with a POMP 1b of 1/10,000 Molar Equivalent

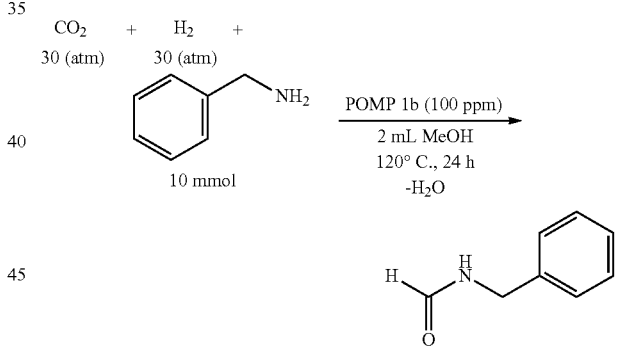

Under an air atmosphere, the benzylamine (10 mmol, 1.07 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a colorless liquid (1.35 g) of N-formyl benzylamine, with a yield of up to 99%.

$^1$H NMR (400 MHz, DMSO) δ 8.51 (br, 1H), 8.14 (s, 1H), 7.33-7.25 (m, 5H), 4.30 (s, 2H) Ppm; $^{13}$C NMR (100 MHz,

CDCl$_3$) δ 165.0 (minor isomer), 161.6 (major isomer), 137.7, 128.9, 128.7, 127.7, 127.5, 127.0, 42.0 ppm.

Embodiment 19: 2-Methylaminopyridine Formylation Reaction Catalyzed with a POMP 1b of 1/10,000 Molar Equivalent

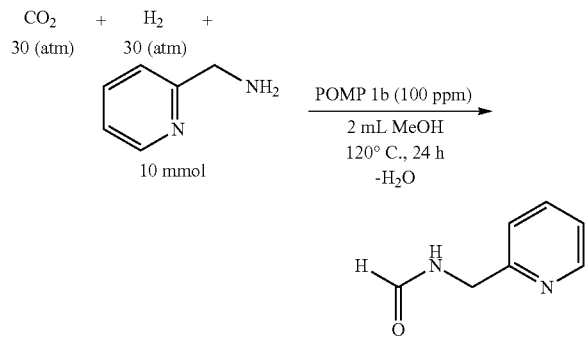

Under an air atmosphere, the 2-methylaminopyridine (10 mmol, 1.08 g), a solid catalyst POMP 1b (100 ppm, 24 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was filtered by a short silica gel column (about 2 cm), and washed with ethyl acetate (5 mL×3); the resulting filtrate was dried with anhydrous sodium sulfate; and the solvent was removed by rotary evaporation to obtain a yellow liquid (1.13 g) of N-(pyridin-2-ylmethyl)formamide, with a yield of up to 83%.

$^1$H NMR (400 MHz, DMSO) δ 8.60 (br, 1H), 8.50 (d, J=4.8 Hz, 0.86H), 8.17 (s, 1H), 7.76 (d, J=4.8 Hz, 1H), 7.30 (m, 2H), 4.41 (s, 1H) ppm; $^{13}$C NMR (100 MHz, CDCl$_3$) δ 165.5 (minor isomer), 161.1 (major isomer), 156.1, 148.9, 137.0, 122.5, 122.1, 47.1 (minor isomer), 43.0 (major isomer) ppm.

Embodiment 20: Amlodipine Base Formylation Reaction Catalyzed with POMP 1b of 1/10,000 Molar Equivalent Under an air atmosphere, the amlodipine base (1 mmol, 0.41 g), a solid catalyst POMP 1b (100 ppm, 2.4 mg) and methanol (2 mL) were added into a stainless steel autoclave with a magnetic stir bar. The autoclave was tightened, purged three times with carbon dioxide, charged with 30 atm carbon dioxide, and then charged with 30 atm hydrogen until a total pressure reaches 60 atm. Afterwards, the reaction system was stirred in an oil bath pan of 120° C. for 24 hours. Upon completion of the reaction, the autoclave was cooled down to the room temperature, and the pressure was released slowly. The resulting mixture was separated by a silica gel column (about 5 cm) to obtain a white solid (0.35 g) of formamide products, with a yield of up to 81%.

$^1$H NMR (400 MHz, CDC$_3$) δ 8.27 (s, 1H), 7.37 (d, J=7.7 Hz, 1H), 7.22 (d, J=7.9 Hz, 1H), 7.14 (dd, J=16.3, 8.9 Hz, 2H), 7.04 (t, J=7.6 Hz, 11H), 5.88 (s, 11H), 5.40 (s, 11H), 4.72 (dd, J=36.6, 15.7 Hz, 2H), 4.04 (ddt, J=10.2, 6.8, 3.6 Hz, 2H), 3.73-3.50 (m, 8H), 2.37 (s, 3H), 1.18 (t, J=7.1 Hz, 3H).

$^{13}$C NMR (100 MHz, CDC$_3$) δ 168.11, 167.16, 161.88, 145.70, 144.90, 144.42, 132.18, 131.38, 129.16, 127.38, 126.88, 103.69, 101.54, 70.24, 67.94, 59.83, 50.77, 37.87, 37.04, 19.22, 14.21.

Those of ordinary skill in the art can understand that the above-mentioned implementation modes are the embodiments for realizing the present invention, whereas in practical applications, various modifications can be made in forms and details without deviating from the spirit and scope of the present invention.

What is claimed is:

1. A method for preparing a formamide compound via hydrogenation of carbon dioxide catalyzed by porous materials, wherein a catalyst that is a porous organometallic polymer as shown in formula (V), and an organic amine compound, as shown in general formula (I), are reacted with carbon dioxide and hydrogen gas under an air atmosphere to form the formamide compound as shown in general formula (II);

the method comprises the following steps:
under the air atmosphere, adding the organic amine compound (I) and the catalyst (V) to a 125 mL autoclave, sealing the 125 mL autoclave, and charging the carbon dioxide and the hydrogen gas with a predetermined pressure to obtain a reaction system;
placing the reaction system in an oil bath, and then stirring and heating the reaction system to perform a reaction at a predetermined reaction temperature for a predetermined reaction time;
slowly releasing the pressure from the autoclave after cooling down, and obtaining the formamide compound by a distillation or a column separation;

wherein a reaction formula is:

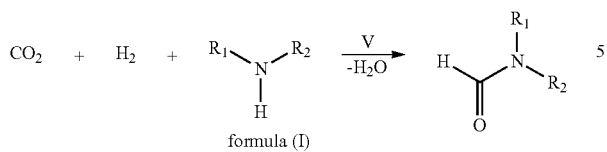

formula (I) → formula (II)

wherein:
R$_1$ is selected from the group consisting of hydrogen, optionally substituted C$_1$-C$_{20}$ alkyl, optionally substituted C$_4$-C$_{10}$ cycloalkyl, optionally substituted C$_6$-C$_{24}$ aryl, optionally substituted C$_6$-C$_{24}$ heteroaryl, optionally substituted C$_7$-C$_{25}$ aryl alkyl, optionally substituted C$_7$-C$_{25}$ heteroaryl alkyl, —(CH$_2$)$_n$—OR$_3$, and —(CH$_2$)$_n$—NR$_4$R$_5$, wherein n=1-8;

R$_2$ is selected from the group consisting of optionally substituted C$_1$-C$_{20}$ alkyl, optionally substituted C$_4$-C$_{10}$ cycloalkyl, optionally substituted C$_6$-C$_{24}$ aryl, optionally substituted C$_6$-C$_{24}$ heteroaryl, optionally substituted C$_7$-C$_{25}$ aryl alkyl, optionally substituted C$_7$-C$_{25}$ heteroaryl alkyl, —(CH$_2$)$_n$—OR$_3$, and —(CH$_2$)$_n$—NR$_4$R$_5$, wherein n=1-8 and R$_1$ and R$_2$ are connected into the optionally substituted C$_4$-C$_{10}$ cycloalkyl;

wherein R$_3$, R$_4$ and R$_5$ are separately selected from the group consisting of hydrogen, optionally substituted C$_1$-C$_{20}$ alkyl, optionally substituted C$_6$-C$_{24}$ aryl, optionally substituted C$_7$-C$_{25}$ aryl alkyl, and optionally substituted C$_7$-C$_{25}$ heteroaryl, wherein R$_4$ and R$_5$ are connected into optionally substituted C$_3$-C$_{10}$ cycloalkyl;

wherein substituted is selected from the group consisting of one or more hydrogens in the group substituted by a substituent selected from the group consisting of halogen, C$_1$-C$_4$ alkyl, C$_1$-C$_4$ halogenated alkyl, C$_2$-C$_6$ alkenyl, C$_2$-C$_6$ alkynyl, C$_1$-C$_6$ alkoxy, hydroxyl, amino, and sulfhydryl;

the porous organometallic polymer as shown in general formula (V) is:

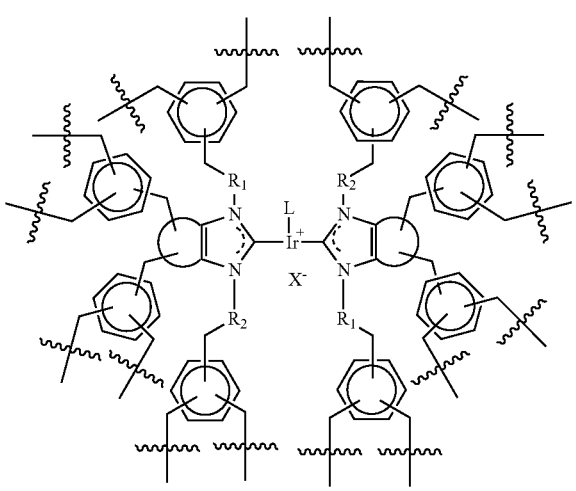

formula (V)

wherein:

=(hetero)aryl and functional group substituted (hetero)aryl;

the N-heterocyclic carbene ligands are benzimidazolylidene, phenanthromidazolylidene, acenaphthoimidazolylidene, pyrenoimidazolylidene, or bibenzimidazolylidene ligands;

X is selected from the group consisting of halogen anion, tetrafluoroborate, hexafluorophosphate, and hexafluoroantimonate;

L is an auxiliary ligand, and the auxiliary ligand is selected from the group consisting of halogen, carbonyl, benzene ring, cyclopentene ring, cyclooctadiene, hydroxyl, water, carbonate, acetate, acetylacetone anion, and phosphine ligand;

R$_1$ and R$_2$ are separately selected from the group consisting of chain alkane groups with a carbon number of 1-12, a cyclic alkane group, benzyl, and aryl with a carbon number of 5-7;

the organic amine compound (I) is an organic primary amine compound or an organic secondary amine compound.

2. The method according to claim 1, wherein a molar ratio of the organic amine compound (I) to the catalyst (V) is (1,000-100,000):1;
the predetermined reaction temperature is 80-150° C., and the predetermined reaction time is 2-160 hours.

3. The method according to claim 1, wherein the predetermined pressure of the hydrogen gas is controlled at 5-40 atm, and the predetermined pressure of the carbon dioxide is controlled at 5-40 atm.

4. The method according to claim 1, wherein the reaction is carried out in at least one organic solvent selected from the group consisting of: DMF, tetrahydrofuran, 2-methyltetrahydrofuran, dioxane, glycol dimethyl ether, tert-butyl methyl ether, benzene, methylbenzene, xylene, methanol, ethanol, isopropanol, and tert-butanol.

5. The method according to claim 1, wherein when the organic amine compound (I) is dimethylamine or an equivalent dimethylamine carbon dioxide salt of the dimethylamine, the formamide compound is DMF.

6. The method according to claim 1, wherein the catalyst (V) is recyclable and reusable.

7. The method according to claim 1, wherein the porous organometallic polymer is prepared by a method comprising the following steps:
at a room temperature, obtaining a reaction mixture by dissolving in an organic solvent a bis-carbene iridium compound shown by general formula (III) and 3-9 equivalents of arene shown by general formula (IV), and slowly adding a cross-linking agent and a Lewis acid as catalysts under nitrogen conditions, and then sealing the reaction mixture;
placing the reaction mixture in an oil bath at 30-80° C. to perform a synthetic reaction for 1-72 hours until the synthetic reaction stops;
after cooling the reaction mixture, performing filtering, washing, Soxhlet extraction and vacuum drying to obtain the porous organometallic polymer shown by the general formula (V);

wherein a reaction formula is:

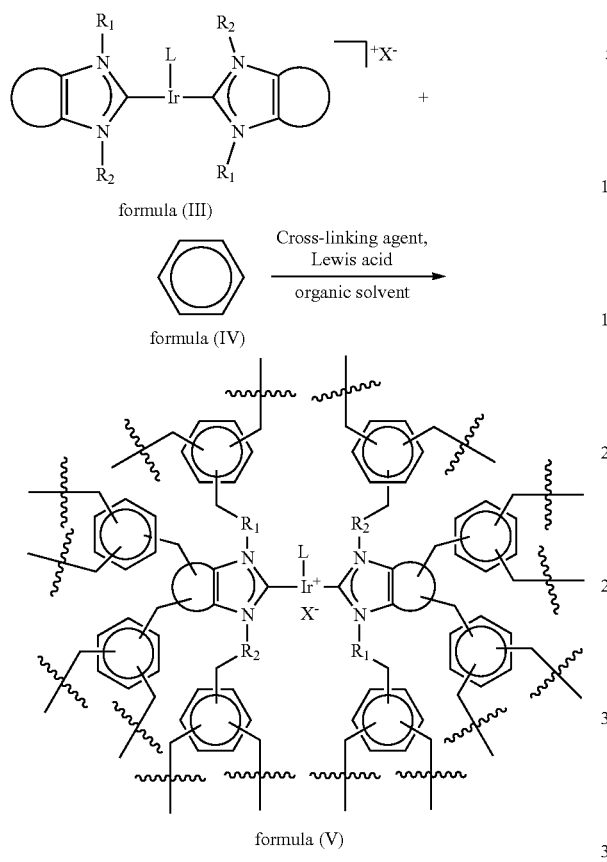

wherein:

=(hetero)aryl and functional group substituted (hetero)aryl;

the N-heterocyclic carbene ligands are benzimidazolylidene, phenanthromidazolylidene, acenaphthoimidazolylidene, pyrenoimidazolylidene, or bibenzimidazolylidene ligands;

X is selected from the group consisting of halogen anion, tetrafluoroborate, hexafluorophosphate, and hexafluoroantimonate;

L is the auxiliary ligand, and the auxiliary ligand is selected from the group consisting of halogen, carbonyl, benzene ring, cyclopentene ring, cyclooctadiene, hydroxyl, water, carbonate, acetate, acetylacetone anion, and phosphine ligand;

$R_1$ and $R_2$ are separately selected from the group consisting of the chain alkane groups with the carbon number of 1-12, and the cyclic alkane groups, benzyl, and aryl with the carbon number of 5-7.

8. The method according to claim 7,
wherein a mass ratio of the arene shown by the general formula (IV) to the bis-carbene iridium compound shown by the general formula (III) is (1-24):1;
a mass ratio of the cross-linking agent to the bis-carbene iridium compound shown by the general formula (III) is (1-100):1.

9. The method according to claim 8, wherein
the cross-linking agent is selected from the group consisting of: dimethoxymethane, trimethyl orthoformate, trimethyl orthoacetate, triethyl orthoformate, triisopropyl orthoformate, dichlorobenzene, dibromobenzene, 1,4-dibenzyl chloride, 1,4-dibenzyl bromide, and carbon tetrachloride;
the organic solvent is selected from the group consisting of dichloromethane, chloroform, carbon tetrachloride, and 1,2-dichloroethane; and
the Lewis acid is selected from iron chloride and aluminum chloride.

10. The method according to claim 2, wherein the reaction is carried out in at least one organic solvent selected from the group consisting of: DMF, tetrahydrofuran, 2-methyltetrahydrofuran, dioxane, glycol dimethyl ether, tert-butyl methyl ether, benzene, methylbenzene, xylene, methanol, ethanol, isopropanol, and tert-butanol.

11. The method according to claim 3, wherein the reaction is carried out in at least one organic solvent selected from the group consisting of: DMF, tetrahydrofuran, 2-methyltetrahydrofuran, dioxane, glycol dimethyl ether, tert-butyl methyl ether, benzene, methylbenzene, xylene, methanol, ethanol, isopropanol, and tert-butanol.

12. The method according to claim 2, wherein when the organic amine compound (I) is dimethylamine or an equivalent dimethylamine carbon dioxide salt of the dimethylamine, the formamide compound is DMF.

13. The method according to claim 3, wherein when the organic amine compound (I) is dimethylamine or an equivalent dimethylamine carbon dioxide salt of the dimethylamine, the formamide compound is DMF.

14. The method according to claim 4, wherein when the organic amine compound (I) is dimethylamine or an equivalent dimethylamine carbon dioxide salt of the dimethylamine, the formamide compound is DMF.

* * * * *